United States Patent [19]

Ohta et al.

[11] Patent Number: 4,478,067
[45] Date of Patent: Oct. 23, 1984

[54] GAS COMPOSITION SENSOR

[75] Inventors: Minoru Ohta; Eturo Yasuda, both of Okazaki; Tomio Kawakami, Nishio; Yoichi Kotanshi, Aichi, all of Japan

[73] Assignee: Nippon Soken, Inc., Nishio, Japan

[21] Appl. No.: 286,346

[22] Filed: Jul. 23, 1981

[30] Foreign Application Priority Data

Jul. 28, 1980 [JP] Japan ................. 55-104049

[51] Int. Cl.³ ............................. G01N 27/12
[52] U.S. Cl. ......................... 73/23; 338/34
[58] Field of Search ............... 338/34, 35; 73/27 R, 73/23; 422/98; 324/71.5

[56] References Cited

U.S. PATENT DOCUMENTS

| 4,210,894 | 7/1980 | Nitta et al. | 338/35 |
| 4,288,774 | 9/1981 | Takami et al. | 338/34 |
| 4,308,518 | 12/1981 | Hattori et al. | 73/27 R |
| 4,322,968 | 4/1982 | Takami et al. | 73/27 R |

FOREIGN PATENT DOCUMENTS

| 493712 | 7/1967 | Japan | 73/23 |
| 136360 | 10/1979 | Japan | 338/34 |

Primary Examiner—Stephen A. Kreitman
Attorney, Agent, or Firm—Cushman, Darby & Cushman

[57] ABSTRACT

A gas composition sensor includes a gas sensor element having an electric resistance value which varies in accordance with the composition of exhaust gases to be sensed, and a pair of electrodes attached to the gas sensor element for detecting the electric resistance value, whereby the resistance value of the gas sensor element is detected to sense the composition of the exhaust gases. A layer of material substantially impervious to the gases is formed on the gas sensor element to extend between the electrodes and surround the electrodes and the layer is also formed on other portions of the electrodes exposed to the exhaust gases.

5 Claims, 10 Drawing Figures

GAS COMPOSITION SENSOR

BACKGROUND OF THE INVENTION

The present invention relates to a gas composition sensor which can be advantageously used with feedback type exhaust gas control systems of the type employing a three-way catalyst.

Systems previously proposed for detecting for example the air-fuel ratio include a method which employs a gas sensor element made from a metal oxide such as $TiO_2$ (titanium dioxide) which is responsive to the composition of exhaust gases and a change in the electric resistance value of the gas sensing element is detected through a pair of electrodes made of platinum or the like and attached to the gas sensor element.

For instance, in the case of a feedback type exhaust gas control system employing a three way catalyst, the air-fuel ratio (A/F) is controlled at the stoichiometric ratio to simultaneously reduce the harmful components or CO, HC and $NO_x$ in the exhaust gases. However, the air-fuel ratio is sometimes increased (enriched) in consideration of the drivability during the periods of starting and warming up of the engine, engine operations where a high load is required, etc. It has been found that in such a case, particularly at low temperatures, a large quantity of soot (carbon) is produced in the exhaust gases and deposited on the surfaces of the gas sensor element.

In other words, if any conductive substance such as carbon is deposited on the surfaces of the gas sensor element, the resistance of the deposit is inserted in parallel with the resistance of the gas sensor element so that the equivalent circuit shown in FIG. 1 is formed and a leakage current is generated between the electrodes of the gas sensor element. Thus, there is the disadvantage that the electrical resistance value presented by the gas sensor element cannot be detected accurately. In FIG. 1, symbol Rs designates the resistance of the gas sensor element, Rc the resistance of the deposit and Rr a reference resistor. For example, the gas sensor element exhibits one Mega ohms at 16 (oxidation side) of a lean air-fuel ratio (A/F) and at 300° C. of the exhaust gas temperature, and 30 Kilo ohms at 13 (reduction side) of a rich A/F. When the resistance of the deposit such as carbon is 100 Kilo ohms, and when the A/F is changed from lean to rich, the electrical resistance of the gas sensor element, which is given by RcRs/(Rc+Rs), changes: 100 Kilo ohms ($\approx 100 \times 100000/100+100000$) at 16 of the A/F ratio and 23 Kilo ohms ($\approx 100 \times 30/100+30$) at 13 of the A/F ratio. As just mentioned, the resistance change in such a case is small and hence it is impossible to measure it.

In consideration of the heat resistance, resistance to chemicals, etc., such noble metal as Pt or Pt-Rh alloy is used for the pair of electrodes for taking out the electric resistance value of the gas sensor element. Also, if the wire diameter is small, the durability of electrodes will not be sufficient even if they are made from any of such materials. Thus, electrodes of about 0.5 mm are usually used. However, since these materials are considerably expensive, this constitutes a main cause of increasing the overall cost of a gas composition sensor.

SUMMARY OF THE INVENTION

With a view to overcoming the foregoing deficiencies in the prior art, it is an object of the present invention to provide a gas composition sensor in which a layer of material substantially impervious to gases is formed on the surfaces of a pair of electrodes and the junction portions of the pair of electrodes and a gas sensor element, whereby preventing reduction in the electric resistance value due to carbon or the like, deterioration of the electrodes due to heat, carbon and atmosphere and breakage of the electrodes and ensuring a sufficient durability.

Thus, the present invention has among its great advantages a fact that a layer of substantially gas impervious material is formed on that side of a sensor element to which electrodes are attached, whereby even if any conductive substance such as carbon is deposited on the surfaces of the sensor element, there is no danger of causing any leakage current between the electrodes and this ensures accurate detection of the electric resistance value exhibited by the sensor element.

Another advantage is that the surfaces of the electrodes are coated with a layer of material substantially impervious to gases, thus reducing the deterioration of the electrodes due to corrosive gases, carbon, etc., in the gases to be sensed and thereby improving the durability of the sensor. Still another advantage is that in contrast to the prior art electrodes made from Pt, Pt-Rh or other alloy and used in the form of relatively thick wires (about 0.5 mm$\phi$) in consideration of the durability, thinner electrodes can be used and they can also be made from inexpensive material, thus making it possible to manufacture the sensor with a reduced cost.

BRIEF DESCRIPTION OF THE DRAWINGS

FIG. 5b is a bottom view of FIG. 5a.

FIG. 6b is a bottom view of FIG. 6a.

FIG. 7b is a bottom view of FIG. 7a.

DESCRIPTION OF THE PREFERRED EMBODIMENTS

The present invention will now be described in greater detail with reference to the illustrated embodiments.

Figure 1:
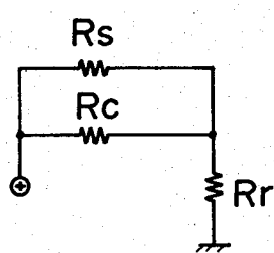
FIG. 1 is an equivalent circuit diagram of a sensor having carbon or the like deposited on its ceramic body.
Figure 2:
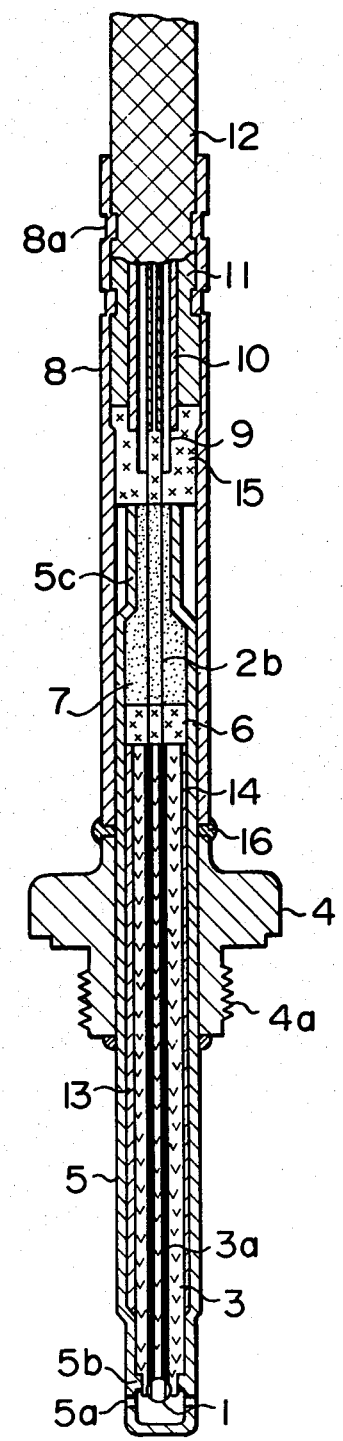
FIG. 2 is a sectional view showing an embodiment of the present invention.
Figure 3:
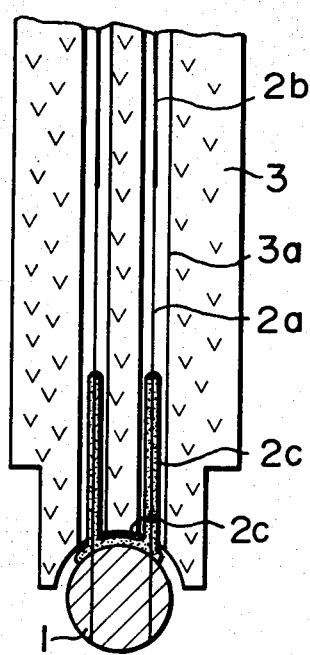
FIG. 3 is a partial enlarged sectional view of FIG. 2.
Figure 4:
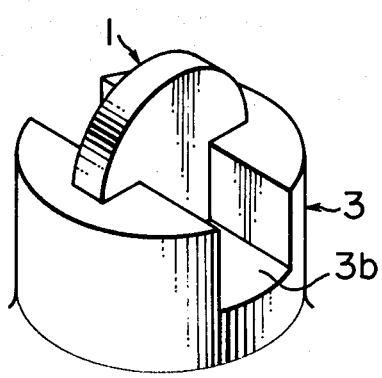
FIG. 4 is a perspective view showing the manner in which the gas sensor element is mounted on the ceramic body in the sensor of FIG. 2.
Figure 5A:
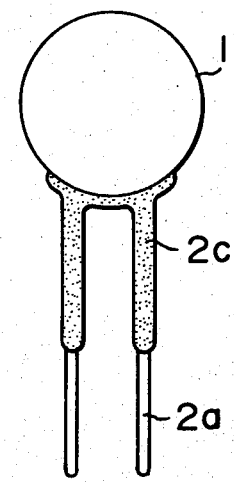
FIG. 5a is a front view of the gas sensor element shown in FIG. 3.

Referring to FIGS. 2 to 5, numeral 1 designates a sensor element comprised of a sinter of metal oxide such as titanium oxide or tin oxide and a catalyst is supported on the sensor element 1. Numeral 2a designates a pair of electrodes made from platinum or the like and partly embedded in the sensor element 1, 2b a pair of sub-lead wires made from heat resisting metal such as stainless steel and electrically conductively connected to the electrodes 2a by welding, and 3 a cylindrical ceramic body formed therethrough with a pair of narrow holes 3a of the same diameter for receiving the electrodes 2a and the sub-lead wires 2b and including a portion having a large outside diameter and located substantially centrally, the body being made from a heat-resisting electrically insulating ceramic, e.g., alumina. Formed in the sensor element side of the ceramic body 3 are a slot for holding the sensor element 1 and a slot 3b for directing the exhaust gases to the sensor element 1. FIG. 4 shows the manner in which the gas sensor element 1 is supported on the ceramic body 3.

Numeral 2c designates a layer of electrically insulating material impervious to gases, such as, glass which is applied to the bottom portion of the sensor element 1 or the portion where the electrodes 2a contact the sensor element 1 to extend between the electrodes 2a and to surround the electrodes 2a. The layer 2c is also applied to the surfaces of the electrodes 2a exposed to the exhaust gases. The method of applying the layer 2c to the sensor element 1 and the electrodes 2a may for example be to spray and deposit a paste of $ZrO_2$—$B_2O_3$ glass by means of a spray gun. Of course, those portions which are not to be coated with the layer 2c are masked by means of a tape or the like. After the tape has been removed, the paste is dried and then baked at a temperature of about 850° C., thus forming the layer 2c.

Numeral 5 designates a pipe which is connected to an exhaust pipe (not shown) via a housing 4. The pipe 5 is fixed to the housing 4 by welding and both of them are made from a heat-resisting corrosion-resisting metal. The pipe 5 is formed with holes 5a for passing the exhaust gases. Numeral 6 designates an inorganic glass sealing material which is placed between the ceramic body 3 and the pipe 5 to close the openings of the holes 3a in the ceramic body 3 and the material 6 is in a solidified form. The glass sealing material 6 ensures the sealing of exhaust gases and the insulation and fixing in place of the sub-lead wires 2b. Numeral 7 designates powder of alumina, magnesium or the like used for ensuring the spacing and electrical insulation between the sub-lead wires 2b. Numeral 8 is a pipe of heat resisting metal which is welded securely to the pipe 5. Numeral 9 designates a pair of lead wires conductively connected by welding to the sub-lead wires 2b, and the outer surface of each of the lead wires 9 is covered with a cover 10 made from a heat-resisting electrically insulating material such as glass wool or heat resisting rubber. The covers 10 are also covered with another cover 11 of the same material, thus electrically insulating the lead wires 9 from each other. Numeral 12 designates a knitted cover of heat resisting metal which is fitted on the outer side of the cover 11. The cover 12 is secured to the pipe 8 by caulking the end portion of the pipe 8 as designated at numeral 8a. The end portion of the pipe 5 is also caulked as designated at numeral 5c, thus increasing the packing density of the internal electrical insulating powder 7. Numeral 13 designates an inorganic adhesive such as Sumiceram (trade name) which is injected into and solidified between the ceramic body 3 and the pipe 5 so as to firmly secure them together. Numeral 14 designates a ring of heat resisting for compressing the adhesive 13. Numeral 15 designates a heat resisting rubber such as silicone rubber which is placed between the pipe 5 and the outermost cover 12 of the lead wires 9 within the pipe 8. The pipe 8 and the housing 4 are welded together at portions designated by numeral 16.

With the construction described above, when any conductive substance such as carbon is produced, carbon deposits on those portions of the sensor element 1 where the layer 2c is not formed and the carbon enters inside the sensor element 1. However, due to the layer 2c formed between the electrodes 2a and made of material which is heat resisting and substantially impervious to gases, the deposition and entry into the sensor element 1 of such conductive substance as carbon are reduced and no leakage current flows between the electrodes 2a, thus preventing any decrease in the electric resistance value of the sensor element 1. Furthermore, since the layer 2c is formed on those surface portions of the electrodes 2a which are likely to be exposed to the gases, the danger of the electrodes 2a being affected by corrosive gases and oxidation reduction gases is reduced and moreover there is no danger of deterioration due to reaction between the electrode materials and carbon, thus preventing the occurrence of any failure due to breakage, etc., of the electrodes 2b.

Figure 6A:
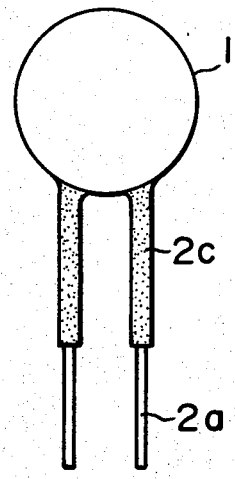
FIG. 6a is a front view showing another embodiment of the present invention.
Figure 6B:
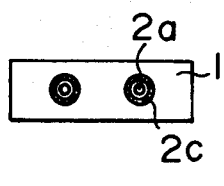

FIGS. 6a and 6b show a second embodiment of the present invention which differs from the first embodiment in that the electrodes 2a are made from Ni-Cr alloy and the layer 2c is made of a dense gas-impervious heat-resisting electrically-insulating material consisting essentially of alumina. The material is made in paste form, applied to the desired portions and then baked at an elevated temperature. Furthermore, the layer 2c is not formed on the center between the electrodes 2a and the layer 2c is formed only on the electrodes 2a and around those portions of the electrodes 2a which are attached to the sensor element 1.

Figure 7A:
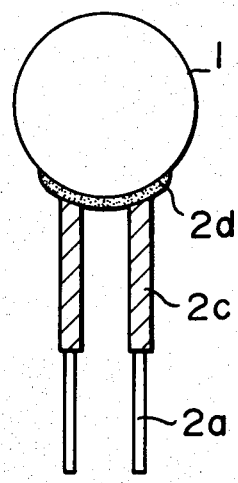
FIG. 7a is a front view showing still another embodiment of the present invention.
Figure 5B:
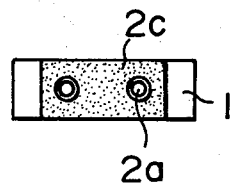
Figure 7B:
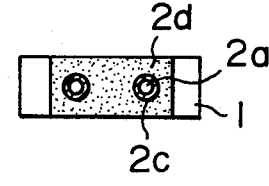

FIGS. 7a and 7b show a third embodiment of the invention which differs from the first embodiment in that electrically insulating and gas impervious layers 2c and 2d of different materials are formed respectively on the electrodes 2a and the sensor element 1. The layer 2c is made from spinel and it is preliminarily formed (prior to molding) by means of plasma spray coating or the like. Then, using the electrodes 2a having the layer 2c formed thereon, the sensor element 1 is formed by powder molding and then baked. Thereafter, the layer 2d is formed by applying $SiO_2$—$Ae_2O_3$—$CaO$ powdered glass by the spray method onto the sensor element 1 so as to extend between the electrodes 2a and surround the electrodes 2a and then baking the material at about 900° C. The electrodes 2a are made from Fe-Ni-Co alloy and the sensor element 1 is made from CoO-MgO alloy.

While the thickness of each of the layers used in the above-described embodiments is dependent on the material of the layer and the materials of the electrodes and the sensor element, it is desired that usually the thickness is in the range of 0.001 to 1 mm and preferably in the range of 0.005 to 0.1 mm. If the thickness is excessively small, the desired effect will be deteriorated. If the thickness is excessively large, the adhesion strength will be deteriorated.

We claim:

1. In a gas composition sensor including a gas sensor element for providing an electric resistance value corresponding to the composition of an exhaust gas to be sensed, a pair of electrodes for detecting said electric resistance value and a ceramic body holding said gas sensor element therein and including a pair of holes formed therethrough and receiving said pair of electrodes to extend therethrough, the improvement wherein at least one layer of a dense material substantially impervious to the exhaust gas is formed on said electrodes and on contacting portions between said electrodes and said gas sensor element, whereby said contacting portions and said electrodes are covered with said layer, thereby to be isolated from the exhaust gas and prevented from contacting thereto.

2. A gas composition sensor according to claim 1, wherein said layer comprises a first and a second layer, and wherein said first layer of gas impervious material is preliminarily formed on said electrodes such that said gas sensor element is powder molded using said electrodes having said first layer formed thereon and then baked, and thereafter said second layer of gas impervious material is formed on said gas sensor element to extend between said pair of electrodes and to surround said electrodes.

3. A gas composition sensor according to claim 1, wherein said layer is formed on said pair of electrodes, contacting portions between said pair of electrodes and said gas sensor element, and the portion of said gas sensor element extending between said pair of electrodes.

4. A gas composition sensor according to claim 1, wherein said layer is formed continuously on the portion extending from the contacting portions between said pair of electrodes and said gas sensor element to said pair of electrodes.

5. A gas composition sensor according to claim 1, wherein said gas-impervious layer consists of selected one of $ZrO_2$—$B_2O_3$ glass and $SiO_2$—$Al_2O_3$—$CaO$ glass.

* * * * *